United States Patent [19]

Wallach et al.

[11] Patent Number: 4,853,228

[45] Date of Patent: Aug. 1, 1989

[54] METHOD OF MANUFACTURING UNILAMELLAR LIPID VESICLES

[75] Inventors: Donald F. H. Wallach, Brookline, Mass.; Jean Philippot, St Clement la Riviere, France

[73] Assignee: Micro-Pak, Inc., Wilmington, Del.

[21] Appl. No.: 78,834

[22] Filed: Jul. 28, 1987

[51] Int. Cl.$^4$ .................................................. A61K 9/62
[52] U.S. Cl. ...................................... 424/450; 436/829
[58] Field of Search ................. 424/94.3, 450; 436/829

[56] References Cited

U.S. PATENT DOCUMENTS

| | | | |
|---|---|---|---|
| 3,957,971 | 5/1976 | Oleniacz | 424/70 |
| 4,133,874 | 1/1979 | Miller et al. | 428/402.2 X |
| 4,182,330 | 1/1980 | Michaels | 424/450 |
| 4,217,344 | 8/1980 | Vanlerberghe et al. | 424/60 |
| 4,235,871 | 11/1980 | Papahadjopoulos et al. | 424/131 |
| 4,241,046 | 12/1980 | Papahadjopoulous et al. | 424/19 |
| 4,247,411 | 1/1981 | Vanlerberghe et al. | 252/316 |
| 4,348,329 | 9/1982 | Chapman | 260/483 |
| 4,356,167 | 10/1982 | Kelly | 424/38 |
| 4,377,567 | 3/1983 | Geho | 424/1 |
| 4,485,054 | 11/1984 | Mezei et al. | 264/4.6 |
| 4,536,324 | 8/1985 | Fujiwara et al. | 264/4.1 |
| 4,544,545 | 10/1985 | Ryan et al. | 424/94.3 |
| 4,551,288 | 11/1985 | Kelly | 264/4.6 |
| 4,564,599 | 1/1986 | Janoff et al. | 436/507 |
| 4,608,211 | 8/1986 | Handjani et al. | 264/4.6 |
| 4,610,868 | 9/1986 | Fountain et al. | 424/1.1 |
| 4,619,913 | 10/1986 | Luck et al. | 514/2 |
| 4,692,433 | 9/1987 | Hostetler et al. | 514/12 |
| 4,695,554 | 9/1987 | O'Connell et al. | 436/528 |
| 4,744,989 | 5/1988 | Payne et al. | 424/491 |
| 4,772,471 | 9/1988 | Vanlerberghe et al. | 424/450 |

FOREIGN PATENT DOCUMENTS

| | | |
|---|---|---|
| 929408 | 6/1963 | European Pat. Off. . |
| 0032578 | 7/1984 | European Pat. Off. . |
| 3410602 | 9/1984 | Fed. Rep. of Germany . |
| 59-106423 | 6/1984 | Japan . |
| 61-207324 | 9/1986 | Japan . |
| 85/01440 | 10/1984 | PCT Int'l Appl. . |
| 1539625 | 1/1979 | United Kingdom . |
| 2147263 | 5/1985 | United Kingdom . |

OTHER PUBLICATIONS

McCutcheon's Emulsifiers & Detergents, MC Publishing Co., 1982, pp. 246 and 77.
Bangham et al. (1965), J. Mol. Biol., 13238-252.
Gregoriadis (1976), New Eng. J. Med. (1976), 295:704-711.
Szoka, Francis and Papahadjopoulos, Demetrios, Procedure for Preparation of Liposomes with Large Internal Aqueous Space and High Capture by Reverse–Phase Evaporation, Proc. Natl. Acad. Sci U.S.A. (1978), 75:4194-4198.
Puisieux and Poly, "Problemes technologiques poses par l'utilisation des liposomes comme vecteurs de substances medicamenteuses, Encapsulation, sterilisation, conservation," in Les Liposomes, Puiseux and Delattre, Eds., Techniques et Documentation La Voisier, Paris (1980), pp. 73-113.
Dousset and Douste-Blazy, "Methodes de preparation des liposomes," in Les Liposomes, Puisieux and Delattre, Eds., Techniques et Documentation La Voisier, Paris (1980), pp. 41-70.
Handjani-Vila, Ribier, and Vanlerberghe, "Les noisomes," in Les Liposomes, Puisieux and Delattre, Eds., Techniques et Documentation La Voisier, Paris (1980), pp. 297-313.
Philippot et al., A Very Mild Method Allowing the Encapsulation of Very High Amounts of Macromolecules into Very Large (1000 nm) Unilamellar Liposomes, Biochem. Biophys. Acta (1983), 734:137-143.
Ribier and Hanjani-Vila, Bilayer Fluidity of Non-Ionic Vesicles, an Investigation by Differential Polarized Phase Fluorometry, Colloids and Surfaces (1984), 10:155-156.
Philippot et al., Extemporaneous Preparation of Large Unilamellar Liposomes, Biochem. Biophys. Acta (1985), 821:79-84.
Baillie et al., The Preparation and Properties of Niosomes–Non-Ionic Surfactant Vesicles, J. Pharm. Pharmacol. (1985), 37:863-868.
Baillie et al., Non-Ionic Surfactant Vesicles, Niosomes, as a Delivery System for the Anti-Leishmanial Drug, Sodium Stibogluconate, J. Pharm. Pharmacol. (1986), 38:502-505.
"Liposomes," Edited by Marc J. Ostro, The Liposome Co., Princeton, N.J., Marcel Dekker, Inc., New York, pp. 246-249 (1983).

Primary Examiner—Johnnie R. Brown
Assistant Examiner—Jean Witz
Attorney, Agent, or Firm—Lahive & Cockfield

[57] ABSTRACT

Disclosed is a new type of unilamellar lipid vesicle made from polyoxyethylene acyl ethers or sorbitan alkyl esters. These unilamellar vesicles are made with easily obtained, relatively inexpensive materials and the vesicles are more stable then conventional unilamellar lipid vesicles. A delivery system for drugs or other molecules is also disclosed.

23 Claims, No Drawings

METHOD OF MANUFACTURING UNILAMELLAR LIPID VESICLES

REFERENCE TO RELATED APPLICATIONS

This application is related to patent application Ser. No. 025,525, filed Mar. 13, 1987.

BACKGROUND OF THE INVENTION

The present invention relates to large lipid vesicular membrane structures having single bilayers surrounding aqueous interiors. More specifically, the present invention relates to unilamellar lipid vesicles having large encapsulation efficiency and captured volume. The large unilamellar vesicles of the invention are useful, for example, as carriers for hydrophilic, biologically active molecules.

Liposomes or lipid vesicles composed of lipid bilayers enclosing an interior aqueous volume are known to be useful as delivery systems for, or carriers of, various substances. There are three general types of liposomes: multilamellar vesicles (MLVs) composed of more than one concentric lipid bilayer separated by a multiplicity of enclosed volumes; small unilamellar vesicles (SUVs) composed of a single lipid bilayer enclosing a single interior volume and having a diameter of less than 0.2μ; and large unilamellar vesicles (LUVs) composed of a single bilayer enclosing a single interior volume and having a diameter of greater than 0.450μ, and preferably greater than 1.0μ.

Lipid vesicles can be characterized by a number of functional properties. Properties of importance include captured volume, a measure of the amount of solvent trapped within the vesicles; and encapsulation efficiency ($E_e$), a measure of the amount of the material to be encapsulated enclosed entirely within the vesicle's internal volume. The captured volume is defined as the concentration of the aqueous fraction inside the vesicle divided by the concentration of lipid in the vesicle, normally expressed as 1/mole lipid. The encapsulation efficiency is defined by the equation $E_e = C'/C \times 1/C_L$, where $C'$ is the final molar concentration of the molecule to be encapsulated within the lipid vesicle, C is the initial molar concentration of the molecule in its solvent, and $C_L$ is the concentration of lipid in the vesicle.

For some uses, e.g., carrying drugs to a specific tissue without dose-related toxicity problems, the vesicles which encapsulate or trap the largest amount of a desired material, and which, upon injection, are the most successful in reaching the targeted tissue are the most valuable. Each type of lipid vesicle is well suited for a different purpose. For example, MLVs are particularly useful for capturing lipophilic materials because of their small aqueous lipid ratio, whereas SUVs, although having low encapsulation efficiencies have the widest tissue access by virtue of their size. LUVs, although very poor in encapsulating hydrophobic or lipophilic materials because of their large aqueous to lipid ratio, have large captured volumes (approximately 35 1/mole lipid) and high encapsulation efficiencies for hydrophilic materials (40–50%). Therefore, LUVs are often the vehicles of choice for transporting hydrophilic, biologically active molecules.

In an effort to create stable, nonantigenic structures having properties similar to natural phospholipid membranes, liposomes have traditionally been synthesized primarily from phospholipids. However, construction of lipid vesicles solely from phospholipids does not accurately recreate the native environment of a membrane since natural membranes also contain proteins and glycoproteins. In addition, phospholipid structures are notoriously unstable in vivo. Factors responsible for this instability include degradation by phospholipases and plasma lipoproteins such as HDL, and by autocatalyzed peroxidation. LUVs, in particular tend to be particularly susceptible to such lytic digestion and peroxidation since they have only a single lipid bilayer surrounding a large aqueous interior.

As well as having the aforementioned stability problems, phospholipids are expensive, making their cost in large scale preparation of liposome operations prohibitive.

In an attempt to solve some of the problems associated with the use of phospholipids in the construction of liposomes, it has been demonstrated that lipid membrane structures, and primarily MLVs, can be prepared from other amphiphilic molecules including fatty acids, dialkyl dimethyl ammonium compounds, and dialkyl amphiphiles with nonionic and zwitterionic head groups, L'Oreal has disclosed the construction of multilamellar vesicles out of synthetic amphiphiles such as alkyl esters of certain polyglycerols and polyoxyethylene, while others have attempted the synthesis of similar vesicles from aliphatic lipids and digalactosyl diglyceride.

Although these efforts have met with varying degrees of success, none have solved all of the foregoing problems.

Accordingly, it is an object of the present invention to provide structurally stable LUVs with high captured volume and high encapsulation efficiency for hydrophilic molecules.

It is an additional object of the invention to provide LUVs which are constructed from lipids which are inexpensive, readily available, biocompatible, and biodegradable.

It is another object of the invention to provide LUVs composed of synthetic, non-phospholipid amphiphilic molecules which are stable, and which are capable of encapsulating hydrophilic molecules.

It is yet another object of the invention to provide LUVs which are capable of encapsulating and transporting hydrophilic molecules.

It is a further object of the invention to provide a delivery system for hydrophilic molecules consisting of an LUV comprising a surfactant, a sterol, a charge-producing amphiphile, and a targeting molecule.

These and other objects and features of the invention will be apparent from the detailed description and claims which follow.

SUMMARY OF THE INVENTION

The present invention features a large lipid vesicular membrane structure having a single lipid bilayer surrounding an aqueous interior. Lipids useful in the construction of these vesicles include surfactants such as polyoxyethylene alkyl ethers, preferably having the structure $$R_1-O-(CH_2-CH_2-O-)_m-H$$

where $R_1$ is $CH_3-(CH_2)_n$, n ranges from 11 to 15, and m ranges from 2 to 4. Although other polyoxyethylene ethers can be used, the most preferred materials are polyoxyethylene (2) cetyl ether and polyoxyethylene (4) lauryl ether.

An alternative group of lipids which are useful in the invention are the sorbitan alkyl esters having the structure

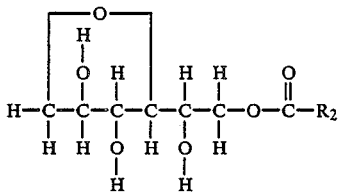

where $R_2$ is $CH_3-(CH_2)_x$, and x ranges from 11 to 15. Although other sorbitan esters can be used, the most preferred materials are sorbitan laurate and sorbitan monopalmitate.

It has been determined that the inclusion of sterols in the construction of the LUVs of the present invention helps to buffer the thermotropic phase transition of the membrane layer, i.e., it enables the lipid membrane structure to be less susceptible to temperature changes in the region of the transition temperature. The sterols also insure optimal vesicle size and increase bilayer stability. Sterols useful in the construction of this invention include cholesterol, its chemical analogs, and its derivatives.

Vesicles of this invention may also include a negative or positive charge-producing amphiphile. Exemplary negative charge-producing materials include dicetyl phosphate, cetyl sulfate, phosphatydic acid, phosphatidyl serine, and mixtures thereof, while exemplary positive charge-producing materials include long chain amines, quaternary ammonium compounds, and mixtures thereof.

The invention may additionally feature a targeting molecule, preferably a hydrophilic molecule. Commonly utilized hydrophilic targeting molecules include immunoglobulins, lectins, and peptide hormones.

The present invention further provides a delivery system for a biologically active hydrophilic material. This system consists of a large unilamellar vesicle having a lipid bilayer surrounding a substantially aqueous interior and enclosing the hydrophilic material. The lipid bilayer is formed of a surfactant selected from the group consisting of polyoxyethylene alkyl ethers and sorbitan alkyl esters, a sterol selected from the group consisting of cholesterol, its chemical analogs, and its derivatives, and a charge-producing amphiphile, and a targeting molecule. Preferably, the lipid bilayer includes approximately 46-48 parts of the surfactant, 46-48 parts of the sterol, 4-8 parts of the charge-producing amphiphile and less than one part of the targeting molecule, most preferably in the ratios of 47.5:47.5:5:<1, respectively. The hydrophilic material enclosed within the lipid bilayer is preferably selected from a group consisting of nucleic acids, immunological adjuvants, enzymes, hormones, lymphokines, blood proteins, pesticides, contrast dyes, and radioactive marker molecules.

The following description and examples will more fully illustrate the invention.

DESCRIPTION

The LUVs of the present invention are preferably manufactured from a subclass of polyoxyethylene alkyl ethers and from certain sorbitan alkyl esters.

Polyoxyethylene alkyl esters for use in the invention have the structure

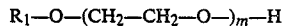

$$R_1-O-(CH_2-CH_2-O-)_m-H$$

wherein $R_1$ is $CH_3-(CH_2)_n$, n ranges from 11 to 17, preferably 11-15, and m refers to the number of polyoxyethylene units in the hydrophilic moiety, commonly 2 to 4. The terminal hydroxyl group can be substituted with a number of functional residues, modifying the properties as desired or for use as a targeting molecule. Selected polyoxyethylene alkyl ethers are available in commerce from a number of manufacturers, for example as the BRIJ series of surfactants manufactured by ICI Americas, Inc.

Of the readily available polyoxyethylene ethers tested to date, polyoxyethylene 2 cetyl ether gives LUVs with the highest (40-50%) encapsulation efficiency, as monitored by the encapsulation of [1,2-$^{14}C$]polyethylene glycol 4,000 (molecule weight=4,000).

The sorbitan acyl esters have the structure

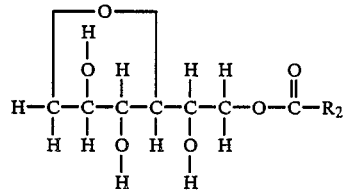

where $R_2$ is $CH_3-(CH_2)_x$, and x ranges from 11 to 15. Although other sorbitan esters can be used, the most preferred materials are sorbitan laurate and sorbitan monopalmitate.

Selected sorbitan esters are available in commerce from many manufacturers, for example, as the SPAN series of surfactants manufactured by ICI Americas, Inc. Sorbitan laurate and sorbitan monopalmitate are preferred to construct LUVs.

Various molecules may be associated with the surfactants for the purpose of modifying the physical properties and permeabilities of the lipid membrane structures. Of particular importance are the sterols such as cholesterol, its chemical analogs, or derivatives which buffer the thermotropic phase transition of the membrane layer, insure optimal size, and increase membrane stability. These effects are enhanced by use of charge-bearing agents. A negative surface charge can be provided by including a small proportion of dicetyl phosphate or cetyl sulfate in the liquid vesicle during formation, and a positive charge by including a small proportion of long chain amines or quaternary ammonium derivatives, such cetyltrimethylammonium.

A number of different targeting molecules can be accommodated in the vesicle to provide LUVs with an affinity for cells having surface architecture recognized by the molecules or for cells bearing receptors for such molecules. Hydrophilic targeting molecules such as immunoglobulins, lectins, and peptide hormones can be coupled to the vesicles in a variety of ways. A preferred method is by covalent linking of the targeting molecule to a palmitate chain and inserting the alkyl chain into the lipid bilayer. Other methods include covalent coupling of the targeting molecule to the amino group of phosphatidylethanolamine in place of palmitate by means of a bifunctional reagent or via spacer molecules to the —CH$_2$OH groups of some of the polyoxyethylene head groups.

Non-limiting examples of the kinds of materials which might be administered to humans, lower animals, and plants by lipid membrane structures described by the present invention are:

(1) Small viruses (e.g. for vaccination), plasmids, and other forms of nucleic acids;
(2) Immunological adjuvants such as muramyl dipeptide;
(3) Enzymes for enzyme replacement therapy and diagnostic testing;
(4) Peptide hormones and growth factors, including insulin, glucagon, pituitary hormones, hypothalamic hormones, angiogenic, epithelial and epidermal growth factors;
(5) Lymphokines which are normally degraded rapidly, such as interleukin-2 and interferon;
(6) Blood proteins, such as hemoglobin, as a basis of artificial blood;
(7) Water soluble plant hormones;
(8) Water soluble pesticides;
(9) Radionucleotides for diagnosis;
(10) Contrast dyes for radiological diagnosis.

To form the LUVs of the present invention, the surfactant capable of forming the large unilamellar lipid membrane structures, together with any other lipophilic substances, including biologically active molecules which are lipophilic, are initially dissolved in an appropriate, generally non-polar solvent or solvent mixture. A 2:1 mixture of chloroform and methanol has been found to be particularly suitable for this purpose. The organic solvent is removed by evaporation under reduced pressure, or from a round-bottom flask under a stream of inert gas, such as nitrogen, generally at between 20° and 60° C.

The residue is then hydrated with an aqueous liquid, typically a buffered solution, which should contain an hydrophilic biologically active molecules which are to be incorporated. Hydration is carried out at a temperature above the transition temperature of the polyoxyethylene alkyl ethers (or sorbitan esters), normally about 39° C. The mixture is solubilized by addition and agitation of a detergent of low molecular weight and high critical micelle concentration, such as octyl glucoside, in 5 to 10-fold molar excess with respect to the lipid.

The solubilizing detergent is then removed, thereby resulting in the formation of LUVs. Detergent removal can be accomplished in a number of ways; e.g., by (1) overnight dialysis against an excess of the aqueous phase buffer, (2) overnight dialysis against a much smaller volume of detergent buffer containing hydrophobic affinity resin, or (3) direct passage over hydrophobic affinity beads.

The LUVs can be separated from unincluded material by exclusion chromatography in which the LUVs and associated material appear in the void volume. The LUVs can then be suspended in any suitable electrolytic buffer for subsequent use.

The following examples will demonstrate the capacity of large unilamellar lipid membrane structures composed primarily of inexpensive readily, available surfactants to act as carriers for molecules of biological importance.

EXAMPLE 1

In this example, large unilamellar vesicles lipid membrane structures are prepared by the following procedure, originally set forth by Philippot et al. utilizing phospholipids. The materials for preparing the large unilamellar vesicular lipid membrane structures and their proportions are given in Table I. A small amount of [1,2-$^{14}$C]polyethylene glycol was included to allow determination of encapsulation efficiency.

TABLE I

| Component | Concentration |
|---|---|
| Polyoxyethylene (2) cetyl ether | 0.0140 mmoles |
| Cholesterol | 0.0120 mmoles |
| Dicetyl phosphate | 0.0015 mmoles |
| Polyethylene glycol 4,000 | 10$^6$ cpm |
| Octyl glucoside | 0.270 mmoles |
| Physiological buffer | 0.5 ml |

In accordance with the method used to construct the vesicles of this invention, the polyoxyethylene (2) cetyl ether (Brij 52, ICI Americas), cholesterol, and dicetyl phosphate were co-dissolved in 0.25 ml of a chloroform:methanol (2:1) solution, and the solvent was removed under a stream of nitrogen from a round-bottom flask. One-half ml of physiological buffer (10 mM Hepes, 1 mM EGTA, 150 mM NaCl, pH 7.4) containing octyl glucoside and [1,2-$^{14}$C]polyethylene glycol 4,000 tracer, was then added, and the mixture solubilized by agitation at 60° C. The clear, solubilized mixture was transferred to a dialysis bag (1 cm wide) permeable to octyl glycoside, and dialyzed over night against 100 ml of the physiological buffer containing 9 mg Bio-Beads SM2 (Biorad, Richmond, CA) /$\mu$mole of octyl glycoside.

The resulting residue constituted a stable, opalescent suspension. Using radioactive polyethylene glycol as a marker for exclusion chromatography on ACA44 (IBF, France) or Sephacryl S1,000 (Pharmacia), the encapsulation efficiently in three experiments was found to lie between 47 and 50%. Electron microscopy revealed LUVs with a diameter of greater than 0.450$\mu$ and a few very large vesicles with diameters greater than 1.00$\mu$. There was no detectable loss of encapsulated material after 24 hours at ambient temperature in physiological buffer. After 1 week at ambient temperature in physiological buffer, there was a loss of about 33%.

Removal of detergent by direct passage of the clear, solubilized mixture over Bio-Beads SM2 gave a lower encapsulating efficiency, approximately 10-20%. These results are comparable to the results of Philippot et al. using the same procedure for phospholipid LUVs. Philippot demonstrated that the rapid extraction procedure for removal of solubilizing detergents yields smaller phospholipid LUVs having lower encapsulation efficiencies.

EXAMPLE 2

In this example, hemoglobin-containing LUVs were prepared. The materials employed and their proportions are given in Table II.

TABLE II

| Component | Concentration |
|---|---|
| Polyoxyethylene (2) cetyl ether | 0.0140 mmoles |
| Cholesterol | 0.0120 mmoles |

TABLE II-continued

| Component | Concentration |
|---|---|
| Dicetyl phosphate | 0.0015 mmoles |
| Polyethylene glycol 4,000 | $10^6$ cpm |
| Octyl glucoside | 0.270 mmoles |
| Human hemoglobin | 0.02 g |
| Physiological buffer | 0.5 ml |

To obtain the hemoglobin for this example, the erythrocytes of freshly drawn human blood were packed by high-speed centrifugation, the buffy coat removed, and the red cells washed three times in physiological saline. The erythrocytes were then lysed by repeated freezing and thawing, and the erythrocyte membranes removed by high-speed ultracentrifugation.

The polyoxyethylene (2) cetyl ether, cholesterol, and dicetyl phosphate were co-dissolved in 0.25 ml of a chloroform:methanol (2:1) solution, and the solvent removed by stream of nitrogen gas. Physiological buffer (0.5 ml) containing the free hemoglobin, the octyl glucoside, and the polyethylene glycol 4,000 tracer, was then added, and the mixture solubilized by agitation at 37° C. The clear, bright red, solubilized mixture was then transferred to a dialysis bag (1 cm wide) permeable to octyl glucoside, and dialyzed against 10 ml buffered medium containing 9 mg Bio-Beads/μmole of octyl glucoside.

After overnight dialysis, the residue constituted a stable, bright-red, opalescent suspension. Upon exclusion chromatography on Biol-Gel A-15m, the hemoglobin-colored LUVs could be seen to elute in the void volume. Measurements of encapsulation efficiency gave values of between 17 and 23%.

EXAMPLE 3

In this example, LUVs were prepared from sorbitan lauryl ester by the method used to construct the vesicles of this invention. The materials used in preparing the LUVs and their proportions are given in Table IV. A small amount of [1,2-$^{14}$C]polyethylene glycol was included to allow determination of encapsulation efficiency.

TABLE III

| Component | Concentration |
|---|---|
| Sorbitan lauryl ester | 0.0140 mmoles |
| Cholesterol | 0.0120 mmoles |
| Dicetyl phosphate | 0.0015 mmoles |
| Polyethylene glycol 4,000 | $10^6$ pm |
| Octyl glucoside | 0.270 mmoles |
| Physiological buffer | 0.5 ml |

The sorbitan lauryl ester (SPAN 20, ICI Americas), cholesterol, and dicetyl phosphate were co-dissolved in 1 ml of a chloroform:methanol (2:1) solution in a round bottomed tube, and the solvent was removed by a stream of nitrogen. Physiological buffer (0.5 ml) containing octyl glucoside and polyethylene glycol 4,000 tracer, was then added, and the mixture solubilized by agitation at 37° C. The clear, solubilized mixture was then transferred to a dialysis bag (1 cm wide) permeable to octyl glucoside and dialyzed against 100 ml buffered medium containing 9 mg Bio-Beads/μ mole of octyl glucoside.

After overnight dialysis, the residue in the dialysis bag constituted a stable, opalescent suspension. Using radioactive polyethylene glycol as a marker for exclusion chromatography on Biogel A-15m, the encapsulation efficiency in three experiments was found to lie between 40 and 50%.

The LUVs prepared from polyoxyethylene (2) cetyl ether or sorbitan esters by dialysis or by exclusion chromatography contain about 10 and 35 liters entrapped volume per mole of lipid. These results are comparable to the results obtained by Philippot et al. (1984) using phospholipids. The values obtained by the dialysis method are considerably larger than those achieved by applying the reverse phase evaporation method described for phospholipids in U.S. Pat. No. 4,235,871.

LUVs which still fall within the scope of the invention can be made from a variety of surfactants. However, a change in the surfactant component may result in a change in the specific encapsulation efficiency of the vesicle.

The invention may be embodied in other specific forms without departing from the spirit and scope thereof. Accordingly, other embodiments are within the following claims.

What is claimed is:

1. A large unilamellar vesicle comprising a surfactant selected from a group consisting of polyoxyethylene alkyl ethers having the structure

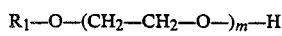

wherein $R_1$ is $CH_3$—$(CH_2)_n$, n ranges from 11 to 15, and m ranges from 2 to 4
and sorbitan alkyl esters having the structure

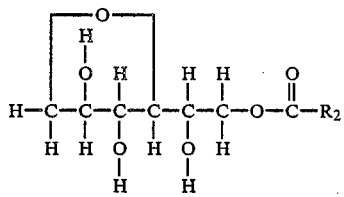

wherein $R_2$ is $CH_3$—$(CH_2)_x$ and x ranges from 11 to 15
and a sterol, whereby said surfactant comprises substantially all the lipid in the structure of said large unilamellar lipid vesicle.

2. The large unilamellar vesicle of claim 1 wherein said polyoxyethylene alkyl ether comprises polyoxyethylene (2) cetyl ether.

3. The large unilamellar vesicle of claim 1 wherein said polyoxyethylene alkyl ether comprises polyoxyethylene (4) lauryl ether.

4. The large unilamellar vesicle of claim 1 wherein said sterol is selected from a group consisting of cholesterol, its chemical analogs, and its derivatives.

5. The large unilamellar vesicle of claim 4 further comprising a charge-producing amphiphile.

6. The large unilamellar vesicle of claim 5 wherein said amphiphile is a negative charge-producing material selected from a group consisting of dicetyl phosphate, cetyl sulphate, phosphatydic acid, phosphatidyl serine, and mixtures thereof.

7. The large unilamellar vesicle of claim 5 wherein said amphiphile is a positive charge-producing material selected from a group consisting of long chain amines, quaternary ammonium compounds, and mixtures thereof.

8. The large unilamellar vesicle of claim 1 further comprising a hydrophilic targeting molecule.

9. The large unilamellar vesicle of claim 8 wherein said hydrophilic targeting molecule is selected from a group consisting of immunoglobulins, lectins, and peptide hormones.

10. The large unilamellar vesicle of claim 1 wherein said sorbitan alkyl ester comprises sorbitan laurate.

11. The large unilamellar vesicle of claim 1 wherein said sorbitan alkyl ester comprises sorbitan monopalmitate.

12. A delivery system for a hydrophilic material, said system consisting of a large unilamellar vesicle having a lipid bilayer surrounding a subtantially aqueous interior, said lipid bilayer comprising a nonphospholipid surfactant, a sterol, a targeting molecule, and a charge-producing amphiphile, said surfactant being selected from a group consisting of polyoxyethylene alkyl ethers having the structure

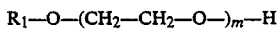

wherein $R_1$ is $CH_3-(CH_2)_n$, n ranges from 11 to 15, and m ranges from 2 to 4, and
sorbitan alkyl esters having the structure

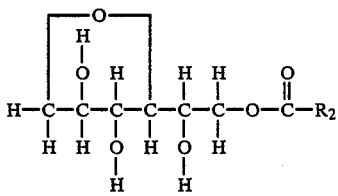

wherein $R_2$ is $CH_3-(CH_2)_x$ and x ranges from 11 to 15
said surfactant comprising substantially all the lipid in the structure of said vesicle.

13. The delivery system of claim 12 wherein said polyoxyethylene alkyl ether comprises polyoxyethylene 2-cetyl ether.

14. The delivery system of claim 12 wherein said polyoxyethylene alkyl ether comprises polyoxyethylene (4) lauryl ether.

15. The delivery system of claim 12 wherein said sorbitan alkyl ester comprises sorbitan laurate.

16. The delivery system of claim 12 wherein said sorbitan alkyl ester comprises sorbitan monopalmitate.

17. The delivery system of claim 12 wherein said sterol comprises cholesterol or its derivatives.

18. The delivery system of claim 12 wherein said amphiphile is a negative charge-producing material selected from a group consisting of dicetyl phosphate, cetyl sulphate, phosphatydic acid, phosphatidyl serine, and mixtures thereof.

19. The delivery system of claim 12 wherein said amphiphile is a positive charge-producing material selected from a group consisting of long chain amines, quaternary ammonium compounds, and mixtures thereof.

20. The delivery system of claim 12 wherein said target molecule comprises a hydrophilic targeting molecule.

21. The delivery system of claim 20 wherein said hydrophilic targeting molecule is selected from a group consisting of immunoglobulins, lectins, and peptide hormones.

22. The delivery system of claim 12 wherein said hydrophilic material is enclosed within said lipid bilayer, said lipid bilayer comprising:
approximately 46–48 parts of said surfactant;
approximately 46–48 parts of a sterol selected from the group consisting of cholesterol, its chemical analogs, and its derivatives;
approximately 4–8 parts of a charge-producing amphiphile; and
less than one part of a targeting molecule.

23. The delivery system of claim 22 wherein said hydrophilic material is selected from the group consisting of nucleic acids, immunological adjuvants, enzymes, hormones, lymphokines, blood proteins, pesticides, contrast dyes, and radioactive marker molecules.

* * * * *